United States Patent
Rus Calborg et al.

(10) Patent No.: US 11,161,149 B2
(45) Date of Patent: Nov. 2, 2021

(54) DEVICE FOR EMITTING TORSIONAL ULTRASONIC WAVES AND TRANSDUCER COMPRISING SAID DEVICE

(71) Applicants: UNIVERSIDAD DE GRANADA, Granada (ES); SERVICIO ANDALUZ DE SALUD, Seville (ES)

(72) Inventors: Guillermo Rus Calborg, Granada (ES); Alicia Valera Martínez, Granada (ES); Elena Sánchez Muñoz, Granada (ES); Francisca Molina García, Granada (ES)

(73) Assignees: Universidad De Grenada, Grenada (ES); Servicio Andaluz De Salud, Seville (ES)

( * ) Notice: Subject to any disclaimer, the term of this patent is extended or adjusted under 35 U.S.C. 154(b) by 679 days.

(21) Appl. No.: 15/747,402

(22) PCT Filed: Jul. 18, 2016

(86) PCT No.: PCT/ES2016/070540
§ 371 (c)(1),
(2) Date: Jan. 24, 2018

(87) PCT Pub. No.: WO2017/009516
PCT Pub. Date: Jan. 19, 2017

(65) Prior Publication Data
US 2018/0214913 A1    Aug. 2, 2018

(30) Foreign Application Priority Data

Jul. 16, 2015  (ES) ............................... ES201500600

(51) Int. Cl.
*B06B 1/06* (2006.01)
*G01N 29/24* (2006.01)
(Continued)

(52) U.S. Cl.
CPC .............. *B06B 1/0611* (2013.01); *A61B 8/00* (2013.01); *B06B 1/04* (2013.01); *G01H 1/10* (2013.01);
(Continued)

(58) Field of Classification Search
CPC ........... B06B 1/0611; B06B 1/04; A61B 8/00; H04R 17/00; G01N 29/043; G01N 11/162;
(Continued)

(56) References Cited

U.S. PATENT DOCUMENTS 4,991,152 A * 2/1991 Letiche ................ B06B 1/0618
                                                                310/337
5,130,953 A * 7/1992 Grosso .................. B06B 1/0618
                                                                29/594
(Continued)

FOREIGN PATENT DOCUMENTS

| CN | 201184875 Y | 1/2009 |
|---|---|---|
| CN | 102012249 A | 4/2011 |
| WO | 2012/172136 A1 | 12/2012 |

OTHER PUBLICATIONS

See attached translated version of WO 2012172136 A1 with InnovationQ Plus IP.com website. (Year: 2012).*

(Continued)

*Primary Examiner* — Shawki S Ismail
*Assistant Examiner* — Htet Z Kyaw
(74) *Attorney, Agent, or Firm* — McCarter & English, LLP (57) ABSTRACT

The invention relates to a wave-emitting device comprising an electromechanical actuator stimulated by a signal generator that allows it to generate torsional waves with a higher amplitude, and to an ultrasonic transducer comprising said device. The use of said devices allows the reconstruction of (Continued)

the structural characteristics of the materials subject to the waves generated by the emitter device.

12 Claims, 4 Drawing Sheets

(51) Int. Cl.
| | |
|---|---|
| A61B 8/00 | (2006.01) |
| H04R 17/00 | (2006.01) |
| G01N 29/04 | (2006.01) |
| G01H 11/08 | (2006.01) |
| B06B 1/04 | (2006.01) |
| G01H 1/10 | (2006.01) |
| G01N 11/16 | (2006.01) |

(52) U.S. Cl.
CPC ............ *G01H 11/08* (2013.01); *G01N 11/162* (2013.01); *G01N 29/043* (2013.01); *G01N 29/24* (2013.01); *H04R 17/00* (2013.01); *G01N 2291/02475* (2013.01); *G01N 2291/02827* (2013.01); *G01N 2291/0426* (2013.01)

(58) Field of Classification Search
CPC ........... G01N 29/24; G01N 2291/0426; G01N 2291/02827; G01N 2291/02475; G01H 11/08; G01H 1/10
USPC ........................................................ 310/333
See application file for complete search history.

(56) References Cited

U.S. PATENT DOCUMENTS

| | | | |
|---|---|---|---|
| 5,761,156 A | | 6/1998 | Reuter et al. |
| 6,310,426 B1 * | | 10/2001 | Birchak ................... B06B 3/04 |
| | | | 310/335 |
| 2004/0120130 A1 * | | 6/2004 | Hensley ............... H05K 9/0015 |
| | | | 361/818 |
| 2004/0209502 A1 * | | 10/2004 | Siahpolo .............. H05K 7/1409 |
| | | | 439/157 |
| 2005/0095351 A1 * | | 5/2005 | Zumeris .................. A61L 29/08 |
| | | | 427/2.1 |
| 2005/0268921 A1 * | | 12/2005 | Zumeris ................. A61B 90/00 |
| | | | 128/898 |
| 2006/0145692 A1 | | 7/2006 | Kim et al. |
| 2007/0232962 A1 * | | 10/2007 | Zumeris ............. A61H 23/0236 |
| | | | 601/2 |
| 2007/0267944 A1 * | | 11/2007 | Ling ....................... G01M 7/06 |
| | | | 310/332 |
| 2008/0309198 A1 * | | 12/2008 | Van Tol ................. H04R 17/00 |
| | | | 310/333 |

OTHER PUBLICATIONS

See attached STIC search report from EIC 2800 searcher Steve Chung on May 21, 2020. (Year: 2020).*
Feltovich et al., Beyond cervical length: emerging technologies for assessing the pregnant cervix. Am J Obstet Gynecol. 2012;207(5):345-354.
Kim et al., Vibration characteristics of piezoelectric torsional transducers. Journal of Sound and Vibration. 2003;264:453-473.
Melchor et al., Torsional ultrasonic transducer computational design optimization. Ultrasonics. 2014;54(7):1950-1962, pre-publication version.
Parra-Saavedra et al., Prediction of preterm birth using the cervical consistency index. Ultrasound Obstet Gynecol. 2011;38(1):44-51.
Ueha et al., Longitudinal-Torsional Composite Transducer and Its Applications. Jpn J Appl Phys. 1987;26:188-190.
Zhou et al., The complex-mode vibration of ultrasonic vibration systems. Ultrasonics. 2002;40(1-8):907-911.
International Search Report and Written Opinion for Application No. PCT/ES2016/070540, dated Oct. 19, 2016, 9 pages.
Supplementary European Search Report for Application No. 16823934.1, dated Feb. 18, 2019, 7 pages.

* cited by examiner

DEVICE FOR EMITTING TORSIONAL ULTRASONIC WAVES AND TRANSDUCER COMPRISING SAID DEVICE

FIELD OF THE ART

The present invention relates to piezoelectric transducers used in the medical diagnosis, industrial monitoring and aeronautics industries, among others. More specifically, the present invention relates to a piezoelectric transducer for generating and receiving torsional ultrasonic and sonic waves in quasi-incompressible solid media (with a Poisson's ratio close to 0.5), gels and certain fluids.

The field of application of the present invention is the non-destructive analyses of materials, and specifically the use of ultrasonic waves for analyzing, preferably, biological tissues. Devices of this type allow obtaining structural information about physical and chemical environments and attaining electrical signals or impulses based on this information, or vice versa.

STATE OF THE ART

Torsional waves are a spatial distribution of transverse waves propagating along an axis in which particle movement occurs along a circumference the center of which is said axis, such that the amplitude of the movement in the generating plane is proportional to the distance from the axis within the diameter of the transducer.

These waves propagate through solid and semi-solid media, but not through perfect liquids, so measuring the speed of sound in media of this type can be very useful for studying their structural characteristics.

A transducer is a device capable of transforming or converting a specific type of input energy into another different type of output energy. These devices include, among others, electromechanical transducers which transform electrical energy into mechanical energy in the form of bidirectional displacements elastically coupled with stresses.

Ultrasonic transducers emit and receive ultrasonic waves, which allows, based on solid mechanics, identifying changes in tissue consistency which may indicate the presence of tumors, and quantifying mechanical or physical changes in the tissue can anticipate certain pathologies sooner than other diagnostic techniques can. The only practical technique today for node screening consists of manual palpation.

The problem with quasi-compressible materials (soft tissues and gels), the Poisson's ratio of which is about 0.5, lies in their bulk modulus and shear modulus being different. P- and S-type waves with different magnitudes propagate in these materials; spurious P-waves that predominate and mask the S-waves are generated, not allowing commercial devices to read the S-waves which provide information about the shear modulus.

Furthermore, the ultrasound technique is a low-cost technique that has no ionizing effects like other diagnostic means such as X-rays.

Conventional ultrasonic transducers emit and receive P-waves and S-waves, where P-waves are longitudinal waves while S-waves are waves that propagate transversely. It is also known that the speed of P-waves is of a far higher order than the speed of S-waves. They are generated by the electrical excitation of piezoelectric crystals arranged in certain directions with respect to the polarization thereof, so they generate compression or shear movements.

By means of elastic wave propagation equations, the propagation of torsional waves is correlated with shear modulus, whereas the propagation of longitudinal waves is correlated with bulk modulus. In soft tissues, the bulk modulus only changes by fractions of a percentage with pathologies, whereas the shear modulus changes by several orders of magnitude, so by using ultrasonic transducers based on torsional waves, a sensitivity far greater than that obtained with ultrasonic transducers based on P-waves and S-waves can be achieved.

Generators for generating torsional waves through windings are known; they, however, have the main drawback of the upper frequency limit as they do not allow emitting ultrasonic waves, and most importantly, they involve contamination with other spurious waves as a result of the complexity of the systems and the coupling between several modes of movement. This is the case of patent document U.S. Pat. No. 5,321,333, which discloses a bilateral device (that generates respective waves at each end) for generating shear movements based on the combination of polarized piezoelectric elements which are attached to a solid rod for transmitting the movement.

Transducers that emit torsional waves like those described in patent document WO 2012172136 are also known. In this patent document, torsional waves are generated as a result of a transmission disk which combines a pair of elastic disks providing the inertia required for reducing the resonance frequency and rigidity for reducing dilatational waves, and a selection of transversely polarized piezoelectric elements which transform the electrical signal into a mechanical movement. Nevertheless, the signal received with the described devices contains too much noise, so its analysis poses serious problems. The lack of quality of this signal does not allow a correct reconstruction of the structural characteristics of the specimen in certain situations.

Techniques for evaluating tissue elasticity [Parra-Saavedra, M., Gómez, L, Barrero, A., Parra, G., Vergara, F., and Navarro, E. (2011) Ultrasound in Obstetrics\&Gynecology 38, 44-51], [Peralta, L, Bochud, N., and Rus, G. (2013) Submitted to J. Mechanical Behavior of Biomedical Materials], [Feltovich, H., Hall, T., and Berghella, V. (2012) American journal of obstetrics and gynecology 207, 345-354] or [Feltovich, H., Hall, T., and Berghella, V. (2012) American journal of obstetrics and gynecology 207, 345-354], such as shear wave elastography (SSI) or cervical consistency index (CCI) and mean gray level histogram, are also known. These techniques have several drawbacks because they generate spurious compressional waves masking the relevant shear waves. Furthermore, the speed which defines cervical stiffness is usually much higher than the maximum shear wave speed given that the latter is limited by the imaging speed of the SSI. On the other hand, the color map of the quasi-esthetic elastography is but a qualitative description of the relative distribution of stresses, without ever being a quantitative description of the actual stiffness of the tissue.

The physical principle for mechanically characterizing the structure of a medium is: a physical magnitude propagates in the form of a wave through the medium to be analyzed, which distorts the wave until it is measured on an accessible surface. The mechanical parameters responsible for wave modification can be deduced from the measurements performed by means of the model-based inverse problem theory. This technique is the most powerful strategy known to date.

Various commercial products are known among elastosonographic devices, such as Fibroscan® (http://www.fibroscan.co.uk/) which only emits a pulse of low-frequency compressional waves, the propagation of which is monitored by means of the elastographic principle using a second higher-frequency compressional wave front.

There is therefore a need to develop alternative transducers capable of emitting and receiving torsional waves with ultrasonic frequency which allow obtaining sensitivity suitable for the detection of irregularities in tissue consistency that have been undetectable until now except by palpation, without the signal being contaminated by spurious waves.

OBJECT OF THE INVENTION

The present invention relates to a device which allows identifying changes in consistency in the materials under study.

Specifically, in a first aspect the invention describes a torsional wave emitter, hereinafter "emitter of the invention", comprising an electromechanical actuator stimulated by a signal generator which allows generating torsional waves with a higher amplitude.

A second aspect of the invention relates to an ultrasonic transducer, hereinafter "transducer of the invention", comprising the emitter of the invention.

This invention is based on the generation and measurement of ultrasounds by means of the non-conventional use of surface and/or shear waves instead of longitudinal waves, given that shear waves are several orders of magnitude more sensitive to changes in the microstructure of the relevant cervical stroma which are closely linked to the viscoelastic shear moduli of the tissue.

Unlike the known devices, particularly those described in patent document WO 2012172136, waves are generated with an electromechanical actuator stimulated by an electrical signal generator and translated into a signal magnitude up to 10 times greater (going from values between 2 and 3 mV to maximum values between 20 and 40 mV), which considerably reduces the noise level, and accordingly facilitates the analysis of the received waves.

Likewise, the emitter of the invention allows emitting torsional waves at several frequencies by means of electrical excitation at said frequencies, the propagation speed of which depends directly on the shear modulus, a main indicator of soft tissue consistency. The use of torsional waves offers greater sensitivity in the detection of irregularities in tissue consistency and has the advantage of eliminating virtually all compressional waves contaminating the signal due to their complex modes of propagation.

The use of ultrasonic waves as a physical magnitude has two fundamental advantages. Firstly, it is a mechanical wave that can be controlled, and is therefore more sensitive to mechanical properties than any other indirect measurement. Secondly, the wave is generated in a low-energy regimen which is more sensitive to changes in tissue consistency than the waves generated at a high-energy regimen are.

The transducer of the invention therefore allows identifying, based on solid mechanics, changes in tissue consistency which may indicate the presence of tumors and any disorder manifesting in the form of said changes in consistency.

DESCRIPTION OF THE DRAWINGS

FIG. 1 depicts the emitter. The contact element (1), the electromechanical actuator (2) and the electrical signal generator (3) can be seen, where (e) represents the axis of the emitter.

DESCRIPTION OF THE INVENTION

Throughout the present description, "specimen" must be understood as the material, preferably a tissue, a tissue culture or a cell culture, through which waves emitted by the transducer are made to pass in order to learn about its structural characteristics (elastic parameters, viscoelastic parameters, microstructural geometry, porous, or energy dissipation models, among others).

For the purpose of the present invention, "electromechanical actuator" will be understood as a device capable of transforming electrical energy into a movement, particularly a rotational movement. In a particular embodiment suitable for this invention, the electromechanical actuator is stimulated with an electrical signal generated by an electrical pulse generator and is capable of transforming said signal into a minimum fraction of a rotation which will be used to generate the wave that is subsequently analyzed.

An example of actuators of this type may consist of an electromagnetic motor.

For the purpose of the present invention, the electromechanical actuator is stimulated by means capable of generating electrical signals or waves, hereinafter "electrical signal generator."

"Electrical signal" is understood as an electrical magnitude the value of which depends on time. For the purpose of the present invention, constant magnitudes will be considered as particular cases of electrical signals.

The electrical signals generated by an electrical signal generator can be periodic signals (sine, square, triangular, "sawtooth"-shaped, etc.). Therefore, by connecting the generator to an actuator which transforms the signal into a rotational movement, said actuator rotates a minimum fraction of a turn depending on the voltage, frequency and/or time between pulses determined by the signal.

Any electronic circuit digitalizing the electrical signals at the desired frequencies can be used as the electrical signal generator. Another example of an electrical signal generator used in the experimental designs of the present invention may be an oscilloscope, as it allows emitting an electrical signal with a variable voltage over a specific time.

"Biocompatible material" will be understood as a material the composition of which does not interfere with or causes degradation of the biological medium in which it is used. These materials are typically used for making devices or elements thereof which must be in direct temporary or prolonged contact with the internal fluids and tissues of the body, such as probes, syringes, prostheses, etc. An example of this material is polylactic acid (PLA).

"Contact element" refers to the part or element that is located in the distal or front part of the transducer and comes into contact with the specimen on which the wave is to be transmitted. The surface of the contact element coming into contact with the specimen must be considerably flat to allow suitable wave transmission.

Emitter of the Invention

In the defined context, a first aspect of the invention consists of an emitter device ("emitter of the invention") for emitting torsional ultrasonic waves comprising (FIG. 1) an electrical signal generator (3) connected to an electromechanical actuator (2) which is in turn attached to the contact element (1), such that when the actuator receives electrical signals, it induces rotational movement of the contact element, and when said contact element comes into contact with the specimen, it induces a torsional wave that goes through said specimen.

Figure 1:
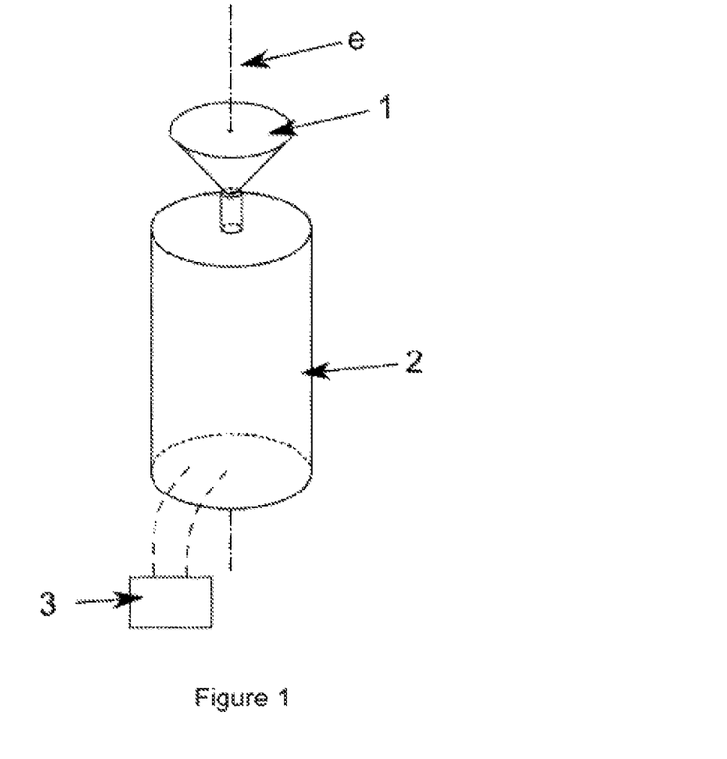

With this configuration, the wave transmitted by the transducer of the invention is a torsional wave, not a longitudinal wave, which improves the quality of the received signals. Unlike other known transducers having a flat wave front progressing in depth, the wave front achieved with the emitter of the invention is a radially-propagating and simultaneously-penetrating wave front (toroidal front).

A signal magnitude with maximum values between 20 and 40 mV can be achieved with this emitter.

Another aspect of the invention relates to the method for emitting torsional waves using the emitter of the invention.

In a particular embodiment, the electrical signal used for stimulating the actuator in this method will be an oscillating signal, more preferably a sinusoidal signal and even more preferably a sine signal.

In this case, the change in voltage over time corresponds to the following function:

$$V(t)=A \cdot \sin(\omega t)$$

where A is the maximum amplitude of the wave, corresponding with the maximum generating voltage.

Figure 2:
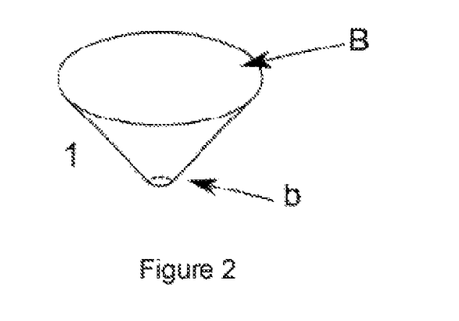
FIG. 2 depicts of a particular embodiment of the contact element (1). (B) represents the larger base of the truncated cone and (b) represents the smaller base.

In another particular embodiment, the contact element has a considerably frustoconical shape (FIG. 2), such that its smaller base (b) is attached to the electromechanical actuator and its larger base (B) is arranged at the distal end of the transducer of the invention so that it comes into contact with the specimen on which shear wave is to be transmitted.

In a preferred embodiment, the contact element is made from a biocompatible material.

In another particular embodiment, the electromechanical actuator is covered by a Faraday cage which eliminates electronic noise. Specifically, the electromechanical actuator is wrapped with a conductive covering acting as a Faraday cage.

Transducer of the Invention

A second aspect of the invention relates to a transducer 10 capable of generating a torsional ultrasonic pulse which propagates by going through the specimen, and it is capable of picking up the distorted pulse after it goes through the specimen. Said transducer 10 ("transducer of the invention") is a transducer comprising the emitter of the invention and means for receiving the distorted signal after it goes through the specimen, hereinafter "receiver."

Figure 3:
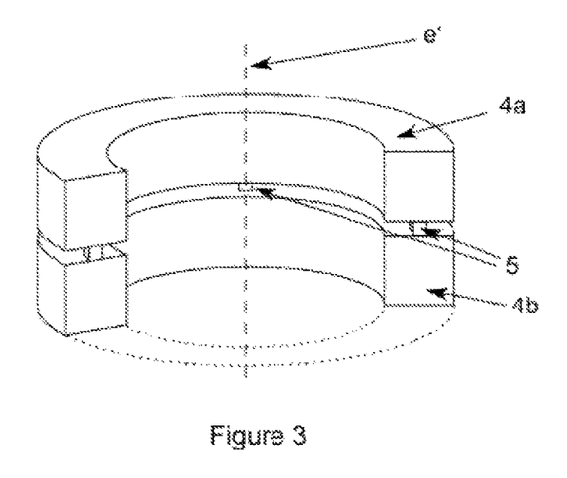
FIG. 3 depicts a section of the receiver in which the rings (front ring 4a, and rear ring 4b) and the piezoelectric elements (5) can be seen. (e') represents the axis of the receiver.

In a particular embodiment (FIG. 3), the receiver of the transducer 10 of the invention comprises two or more piezoelectric elements (5) located equidistant from one another and placed between two rings (4a and 4b). The rings are preferably made from a non-conducting material, more preferably a biocompatible material, such that each piezoelectric element is in contact with two electrodes of different charges, arranged perpendicular to the polarization of said piezoelectric elements.

Figure 4:
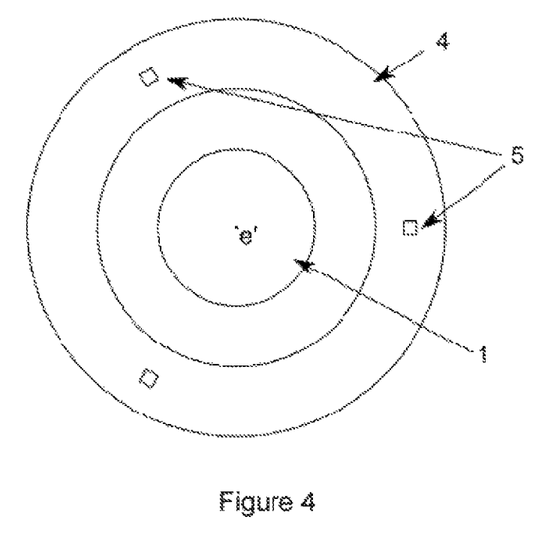
FIG. 4 depicts the arrangement of the emitter and the receiver in which the contact element (1), the rings (4) and the piezoelectric elements (5) can be seen. (e') represent the axis of the receiver which coincides with the axis of the emitter in this arrangement.

In their preferred arrangement, (FIG. 4), the axis of rotation (e') of the rings (4) of the receiver and the axis (e) of the contact element (1) must coincide with one another, the emitter being located inside the rings.

Figure 5:
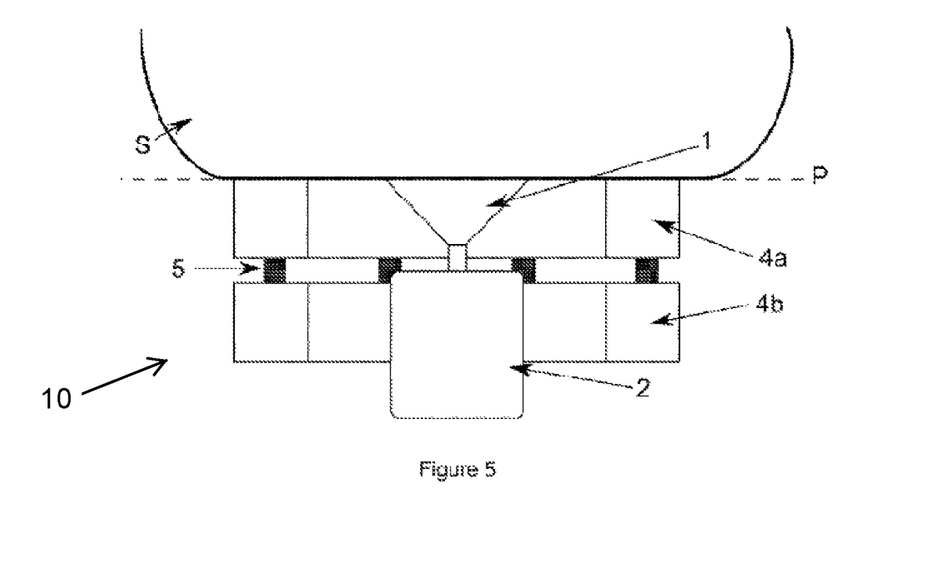
FIG. 5 schematically depicts the contact between the transducer and the specimen (S). (P) represents the plane of contact, (1) the contact element, (2) the electromechanical actuator, (4a) the front ring, (4b) the rear ring and (5) the piezoelectric elements (5).

Likewise (FIG. 5), in order for both the emitter and the receiver to be in contact with the specimen (S), the outer face of one of the rings, called the front ring (4a), and the flat surface of the contact element (1) must be located on the same plane (P) (plane of contact).

In another particular embodiment, the faces of the rings coming into contact with the piezoelectric elements (inner faces) will be covered with a conductive silver resin, which will act most of the time as an electrode on the attachment faces between the piezoelectric elements and the rings, such that each ring will act independently as the anode and cathode.

Figure 6:
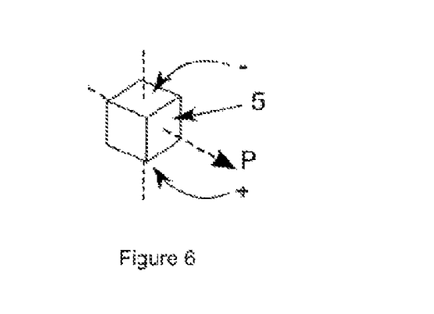
FIG. 6 depicts a piezoelectric element (5) and the direction of polarization (P) thereof.

Polarization, which is understood to be the direction between the positive and negative charges of the electrode, of the piezoelectric elements can be carried out in two different ways. In a preferred embodiment, the polarization is parallel to the axis, the electrodes being arranged on side faces of said piezoelectric elements; in a more preferred embodiment, the polarization (P) is perpendicular to the axis in the radial direction, the electrodes being arranged in the attachment between said piezoelectric elements and the rings (FIG. 6).

In a preferred embodiment, the piezoelectric elements (5) are made from piezoelectric ceramic PZT-4 or PZT-5.

The transmission and reception elements of the transducer 10 are arranged inside a casing (7, FIG. 7) which, in addition to protecting the transducer against physical impacts (such as falls or scratches), assures device functionality as each element is fixed in its correct position.

In the particular case in which the receiver of the transducer of the invention is formed by concentric rings, the casing must allow the emitter to remain located inside said rings, such that the axes of rotation thereof.

In a preferred embodiment, the casing is made from polylactic acid (PLA).

Figure 7:
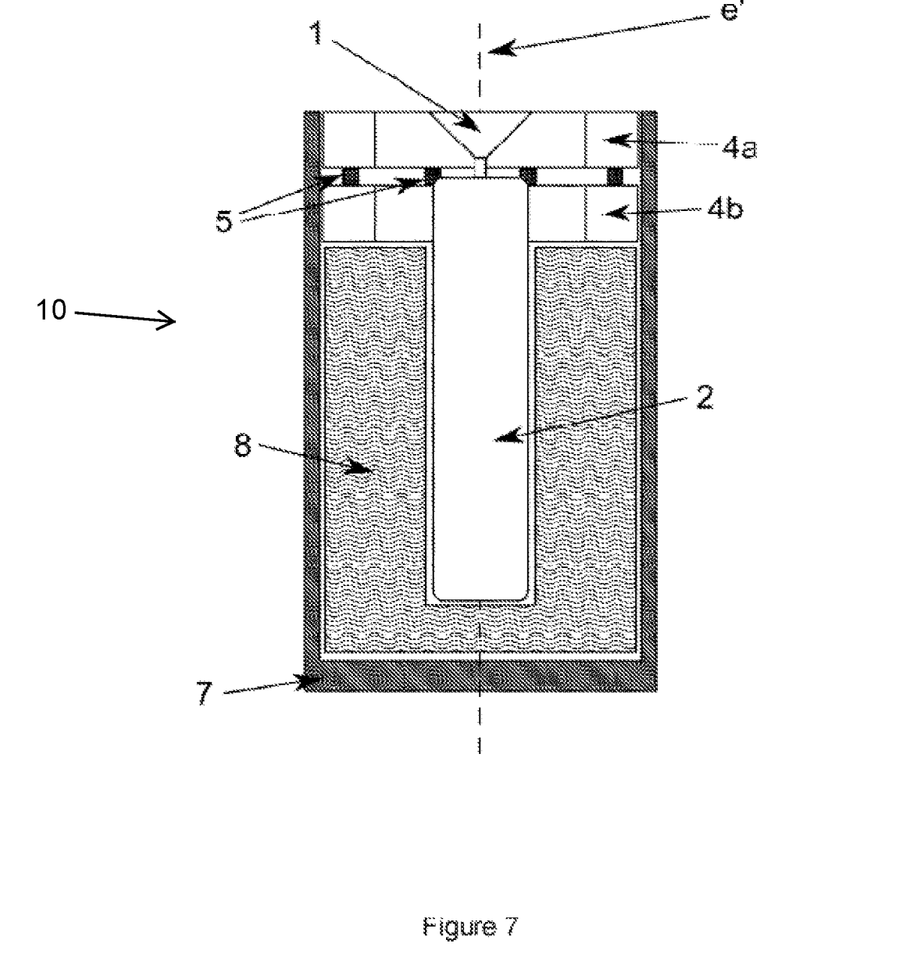
FIG. 7 shows a section of the transducer of the invention in which there can be seen the arrangement of the emitter, where (1) represents the contact element and (2) the electromagnetic actuator, with respect to the receiver, (4a) and (4b) represent the upper and rear rings and (5) the piezoelectric elements, and the arrangement thereof inside a casing (7) together with the attenuating elements (8).

Optionally, in another particular embodiment the transducer of the invention further comprises an attenuating element (8), preferably an attenuating resin, fixed to the outer face of the ring that is the farthest away from the area of contact with the specimen, in order to prevent the propagation of torsional waves in the direction opposite that of the specimen, and therefore also preventing energy losses. The effective emission of torsional waves thereby occurs on only one face of the transducer, i.e., the face put in contact with the specimen, the oscillation of the rear face being cancelled by means of the attenuating element. Furthermore, the cancellation of the emitted waves in the direction opposite the direction of the specimen means that the emitted waves require a simpler processing, as a cleaner signal is achieved.

In an even more particular embodiment, the transducer of the invention which allows emitting and receiving torsional waves comprises the following elements:

An emitter comprising:
  an electrical signal generator
  an electromechanical actuator connected to the electrical signal generator and covered by a Faraday cage,
  a contact element attached to the electromechanical actuator such that when the actuator receives electrical signals, it induces rotational movement of the contact element; and A receiver comprising:
  two rings preferably made from a non-conducting material,
  two or more piezoelectric elements arranged between the preceding rings and separated equidistantly.

A casing which allows the emitter to remain located inside the receiver such that the axes of the contact element and the rings coincide with one another and the outer part of said contact element and the outer face of one of the rings remain on the same plane, such that they can come into contact with the specimen.

Furthermore, in another more preferred embodiment the transducer is completed with a latex membrane adapted to the shape of the device, assuring the dissipation of the wave travelling therethrough with an adapted involution between the emitter and the receiver.

Mechanical Parameter Reconstruction Method

To reconstruct the mechanical parameters of the specimen, a computational model which is combined with an "inverse problem" algorithm that receives as input the measurements of mechanical parameters such as Young's modulus relating to sample compressibility, the attenuation of waves transmitted through said samples, as well as the bulk and/or shear moduli of the ultrasonic wave with the specimen, is used.

In particular, the mechanical properties of the specimen are reconstructed by means of comparing the received wave (subtracting the wave travelling through the capsule) with a wave simulated from the excitation signal of the electromechanical actuator, taking into account the internal delay characteristic of the system referring to the actual transformation of the wave from the time the pulse is emitted in the actuator until the time it reaches the end of the biocompatible element in contact with the specimen. Like the wave transmitted through the capsule, this internal delay is independent of the specimen.

EMBODIMENT

The embodiment of the transducer object of the invention with the following dimensions and materials is proposed in a non-exclusive manner.

The transducer comprises:
  A frustoconical-shaped contact element made from PLA, the larger base of which will come into contact with the specimen and the smaller base of which is fixed to the shaft of the electromechanical actuator.
  An electromechanical actuator consisting of a miniaturized motor 4 mm in diameter, fixed to the rear end (smaller base) of the contact element.
  An oscilloscope connected to the electromechanical actuator such that it transmits an electrical signal which the actuator transforms into rotational movement which the contact element converts into shear wave when it comes into contact with the specimen.
  An aluminum sheet arranged forming a covering for the electromechanical actuator and its conductive elements, and connected to the negative cable of the electromechanical actuator, such that it acts as a Faraday cage.
  A first ring made from a plastic material, preferably PLA, having an outer diameter of 17 mm, an inner diameter of 13 mm and a thickness of 5 mm.
  A second ring made from a plastic material, preferably PLA, having an outer diameter of 17 mm, an inner diameter of 13 mm and a thickness of 5 mm, placed parallel to the first ring.
  A conductive covering located on the inner faces of each ring, such that it is in contact with the electrodes and works as an electrode.
  4 piezoelectric elements made from piezoelectric ceramic PZT-4 or PZT-5, with dimensions of 1.5×1.5×2.5 mm, fixed to the rings. These piezoelectric elements are polarized in the circumferential direction parallel to the rings, whereas the electrodes are located in the attachment between the piezoelectric elements and the inner face of the rings.

The piezoelectric elements and wiring are attached to the electrodes with a conductive silver resin.

The electromechanical actuator, which induces a torsional movement, is attached to its aluminum covering with a conductive silver resin.

The entire assembly is introduced in a casing adapted to the diagnostic device and made from PLA assuring the functionality of the device with its corresponding emitter attenuating elements with respect to the receiver and maintaining the relative arrangement between the emitter and the receiver such that their axes of rotation coincide with one another and the front part of the contact element and the outer part of the front disk remain on the same plane.

For hygienic purposes, the transducer is completed with a latex membrane adapted to the shape of the device. The use of latex assures the dissipation of the wave travelling through it with an adapted involution between the emitter and the receiver.

The invention claimed is:

1. A transducer, comprising:
   an emitter device for emitting torsional ultrasonic waves, the emitter device comprising:
   an electromechanical actuator;
   a contact element; and
   an electrical signal generator connected to the electromechanical actuator which is, in turn, attached to the contact element that comes into contact with a specimen, such that when the actuator receives electrical signals, it induces rotational movement of the contact element, and when said contact element comes into contact with the specimen, it induces torsional ultrasonic waves that go through said specimen wherein the contact element has a frustoconical shape including a smaller base attached to the electromechanical actuator and a larger base arranged at a distal end of the transducer and configured to come into contact with the specimen;
   a proximal ring and a distal ring made from a non-conducting material; and
   an attenuating element fixed to an outer face of the proximal ring that is farthest away from an area where the contact element contacts the specimen.

2. The transducer of claim 1, further comprising a Faraday cage configured to cover the electromechanical actuator and eliminate or reduce electronic noise.

3. The transducer of claim 1, further comprising two or more piezoelectric elements located equidistant from one another and placed between the proximal ring and the distal ring for receiving a signal that has passed through the specimen.

4. The transducer of claim 3, wherein a polarization of the two or more piezoelectric elements is perpendicular to an axis of rotation of the proximal ring and of the distal ring and in a radial direction relative to the axis of rotation of the proximal ring and of the distal ring.

5. The transducer of claim 1, wherein an axis of rotation of the proximal ring and of the distal ring coincides with an axis of rotation of the electromechanical actuator.

6. The transducer of claim 1, wherein an outer face of the distal ring and a surface of the contact element that comes into contact with the specimen are located on a same plane.

7. A method for emitting torsional waves using the transducer of claim 1, the method comprising stimulating the electromechanical actuator using an electrical signal produced by the electrical signal generator.

8. The method according to claim 7, wherein the electrical signal used for stimulating the electromechanical actuator is an oscillating signal.

9. The method according to claim 8, wherein the electrical signal used for stimulating the electromechanical actuator is a sinusoidal signal.

10. The method according to claim 8, wherein the electrical signal used for stimulating the electromechanical actuator is a sine signal.

11. The method of claim 7, wherein the method further comprises in vitro reconstruction of mechanical properties of the specimen.

12. The transducer of claim 1, wherein the attenuating element comprises an attenuating resin.

\* \* \* \* \*